(12) United States Patent
delaHoussaye et al.

(10) Patent No.: US 10,192,410 B1
(45) Date of Patent: Jan. 29, 2019

(54) SYSTEM FOR PROVIDING NOTIFICATION OF A STATUS OF A PATIENT EXAMINATION AND RELATED METHODS

(71) Applicant: SEECA MEDICAL, INC., Houma, LA (US)

(72) Inventors: Arthur J. delaHoussaye, Houma, LA (US); Holly K. Acosta, Lockport, LA (US); James D. Authement, Montegut, LA (US); Talia A. Rhodes, Houma, LA (US)

(73) Assignee: Seeca Medical, Inc., Houma, LA (US)

( * ) Notice: Subject to any disclaimer, the term of this patent is extended or adjusted under 35 U.S.C. 154(b) by 0 days.

(21) Appl. No.: 15/988,412

(22) Filed: May 24, 2018

Related U.S. Application Data (60) Provisional application No. 62/653,684, filed on Apr. 6, 2018.

(51) Int. Cl.
  *G08B 5/36* (2006.01)
  *G16H 40/20* (2018.01)
  *G16H 10/60* (2018.01)

(52) U.S. Cl.
  CPC ............ *G08B 5/36* (2013.01); *G16H 10/60* (2018.01); *G16H 40/20* (2018.01)

(58) Field of Classification Search
  CPC combination set(s) only.
  See application file for complete search history.

(56) References Cited

U.S. PATENT DOCUMENTS

| | | | | |
|---|---|---|---|---|
| 4,937,743 A * | 6/1990 | Rassman | ............... | G06Q 10/06 705/7.22 |
| 5,059,943 A * | 10/1991 | LoBello | .................. | G08B 5/36 340/309.4 |
| 5,760,704 A * | 6/1998 | Barton | .................. | G16H 40/20 340/286.07 |
| 5,831,534 A * | 11/1998 | Mooney | ................ | G08B 21/22 340/573.1 |
| 8,469,713 B2 | 6/2013 | Kron et al. | | |
| 8,669,716 B2 | 3/2014 | Recker et al. | | |
| 2012/0044067 A2* | 2/2012 | Crum | .................... | G06Q 10/02 340/521 |
| 2015/0149190 A1 | 5/2015 | Chace et al. | | |
| 2015/0149206 A1 | 5/2015 | Jester et al. | | |
| 2016/0157789 A1* | 6/2016 | Nicolaus | ............... | A61B 5/747 340/573.1 |

OTHER PUBLICATIONS

Mi.Light; "Welcome to scintillating future—Milight"; http://www.milight.com/; Sep. 28, 2017 (as disclosed in WayBack Machine portal); last accessed on Nov. 30, 2017; 4 pages.

* cited by examiner

*Primary Examiner* — Travis R Hunnings
(74) *Attorney, Agent, or Firm* — McGlinchey Stafford; R. Andrew Patty, II (57) ABSTRACT

Systems for providing a notification about a status of a patient examination and related methods are described in this disclosure.

20 Claims, 7 Drawing Sheets

SYSTEM FOR PROVIDING NOTIFICATION OF A STATUS OF A PATIENT EXAMINATION AND RELATED METHODS

CROSS-REFERENCE TO RELATED APPLICATIONS

This application claims the benefit of U.S. Provisional Application No. 62/653,684, filed Apr. 6, 2018.

STATEMENT REGARDING FEDERALLY SPONSORED RESEARCH OR DEVELOPMENT

Not Applicable.

TECHNICAL FIELD

The present disclosure relates to systems and methods for providing notification about a status of a patient examination.

BACKGROUND

This section introduces information from the art that may be related to or provide context for some aspects of the techniques described herein and/or claimed below. This information is background facilitating a better understanding of that which is disclosed herein. Such background may include a discussion of "related" art. That such art is related in no way implies that it is also "prior" art. The related art may or may not be prior art. The discussion is to be read in this light, and not as admissions of prior art.

Managing patient flow for a medical practice can be a challenge. Typically, patients do not like waiting in an examination room any longer than is necessary, and most physicians and medical practice personnel want to know the status of the medical examination before entering the examination room. Generally, many medical practices utilize a "flag system" to manage patient flow. The "flag system" utilizes multiple flags placed outside an examination room. Each flag is assigned a different color, which indicates the status of a patient examination. In the "flag system", the medical practice personnel or physician manually selects the flag color based on the status of the patient examination, and then actuates or otherwise displays the selected flag so that it is in the active state. In this manner, the physician and other medical practice personnel can determine the status of a patient examination by viewing the flag outside of the examination room.

While there are many benefits to the "flag system", there are drawbacks. As an example, "flag system" often does not provide the status of a patient examination in real-time, substantially real-time, or asynchronously. For example, in a typical medical practice, medical personnel, such as a nurse or technician, bring a patient to the examination room for an initial assessment. The initial assessment may involve such tasks as taking the vitals of the patient (e.g., blood pressure, height, and weight) and the initial medical history of the patient. Meanwhile, the physician is waiting for the medical personnel to finish the initial assessment. The physician typically has no way of determining the status of the initial assessment and thus may begin another task while waiting for the nurse or technician to finish the initial assessment, even though it might be completed imminently. As a result, the patient may have to wait several minutes before the physician finishes the task and can enter the examination room to see the patient. Further, the medical practice personnel or physician may neglect to change the flag so it corresponds to the real-time status of the patient examination and thus the physician and others may incorrectly identify the current status of the patient examination. As a result, the efficiency of the patient flow can be decreased, which can lead to wasted time for the patient, physician, and medical practice personnel as well as increased costs.

Contained herein is a disclosure directed to resolving, or at least reducing, one or more of the problems mentioned above, or other problems that may exist in the art.

NON-LIMITING BRIEF SUMMARY OF THE INVENTION

The present disclosure relates to systems and methods for providing notification about the status of a patient examination.

An aspect of the invention includes a system for providing notification about the status of a patient examination. The system comprises at least one visual indicator; at least one control device in operative communication with the at least visual indicator; one or more data stores; one or more processors in operative communication with the one or more data stores and the at least one control device; and one or more tangible non-transitory computer readable storage media upon which is encoded machine-readable code that when executed is configured so that the system carries out a method comprising receiving from one or more computer interfaces and storing in one or more of the data stores, data comprising information indicative of the status of the patient examination; generating a signal indicative of the status of the patient examination using the one or more processors; sending the signal indicative of the status of the patient examination to the at least one control device over at least one communication network using the one or more processors; and changing a control parameter of the at least one visual indicator based on the signal indicative of the patient examination status using the at least one control device so as to cause the at least one visual indicator to reflect the status of the patient examination.

One or more aspects of the invention include the system of the preceding paragraph wherein the at least one visual indicator comprises one or more light sources.

One or more aspects of the invention include the system of the preceding paragraph wherein the at least one control device is configured to control the hue of light emitted by the one or more light sources, based on the signal indicative of the status of the patient examination.

One or more aspects of the invention include the system of any preceding paragraph wherein the at least one visual indicator is positioned outside of a patient examination room.

One or more aspects of the invention include the system of any preceding paragraph wherein the at least one visual indicator reflects the status of the patient examination in real-time or in substantially real-time.

One or more aspects of the invention include the system of any preceding paragraph wherein the visual indictor comprises one or more electronic devices.

One or more aspects of the invention include the system of any preceding paragraph wherein the data comprising information indicative of the status of the patient examination is obtained or derived from an electronic medical record.

Another aspect of the invention includes a tangible non-transitory computer readable storage medium having computer executable code thereon, that when executed by one or more processors causes the one or more processors to carry out a method for providing notification about the status of a patient examination. The method comprises receiving from one or more computer interfaces and storing in one or more data stores, data comprising information indicative of the status of the patient examination; generating a signal indicative of the status of the patient examination using one or more processors; sending the signal indicative of the status of the patient examination to at least one control device over at least one communication network using the one or more processors; and changing a control parameter of at least one visual indicator based on the signal indicative of the patient examination status using the at least one control device so as to cause the at least one visual indicator to reflect the status of the patient examination.

One or more aspects of the invention include the tangible non-transitory computer readable storage medium of the preceding paragraph wherein the at least one visual indicator comprises one or more light sources.

One or more aspects of the invention include the tangible non-transitory computer readable storage medium of the preceding paragraph wherein the at least one control device is configured to control the hue of light emitted by the one or more light sources, based on the signal indicative of the status of the patient examination.

One or more aspects of the invention include the tangible non-transitory computer readable storage medium of any preceding paragraph wherein the at least one visual indicator is positioned outside of a patient examination room.

One or more aspects of the invention include the tangible non-transitory computer readable storage medium of any preceding paragraph wherein the at least one visual indicator reflects the status of the patient examination in real-time or in substantially real-time.

One or more aspects of the invention include the tangible non-transitory computer readable storage medium of any preceding paragraph wherein the visual indictor comprises one or more electronic devices.

Another aspect of the invention includes a method for providing notification about the status of a patient examination. The method comprises receiving from one or more computer interfaces and storing in one or more data stores, data comprising information indicative of the status of the patient examination; generating a signal indicative of the status of the patient examination using one or more processors; sending the signal indicative of the status of the patient examination to at least one control device over at least one communication network using the one or more processors; and changing a control parameter of at least one visual indicator based on the signal indicative of the patient examination status using the at least one control device so as to cause the at least one visual indicator to reflect the status of the patient examination.

One or more aspects of the invention include the method of the preceding paragraph wherein the at least one visual indicator comprises one or more light sources.

One or more aspects of the invention include the method of the preceding paragraph wherein the at least one control device is configured to control the hue of light emitted by the one or more light sources, based on the signal indicative of the status of the patient examination.

One or more aspects of the invention include the method of any preceding paragraph wherein the at least one visual indicator is positioned outside of a patient examination room.

One or more aspects of the invention include the method of any preceding paragraph wherein the at least one visual indicator reflects the status of the patient examination in real-time or in substantially real-time.

One or more aspects of the invention include the method of any preceding paragraph wherein the visual indictor comprises one or more electronic devices.

While multiple embodiments are disclosed, still other embodiments will become apparent to those skilled in the art from the following detailed description. As will be apparent, certain embodiments, as disclosed herein, are capable of modifications in various obvious aspects, all without departing from the spirit and scope of the claims as presented herein. Accordingly, the drawings and detailed description are to be regarded as illustrative in nature and not restrictive.

BRIEF DESCRIPTION OF THE SEVERAL VIEWS OF THE DRAWINGS

The claimed subject matter may be understood by reference to the following description taken in conjunction with the accompanying figures, in which like reference numbers or symbols refer to like parts or components illustrated therein, and in which:

The accompanying figures illustrate specific embodiments. However, it is to be understood that these embodiments are not intended to be exhaustive, nor limiting of the disclosure. These specific embodiments are but examples of some of the forms in which the disclosure may be practiced.

DETAILED DESCRIPTION

This disclosure describes systems for providing notification about a status of a patient examination and related methods.

1. System for Providing Notification About the Status of a Patient Examination

Figure 1:
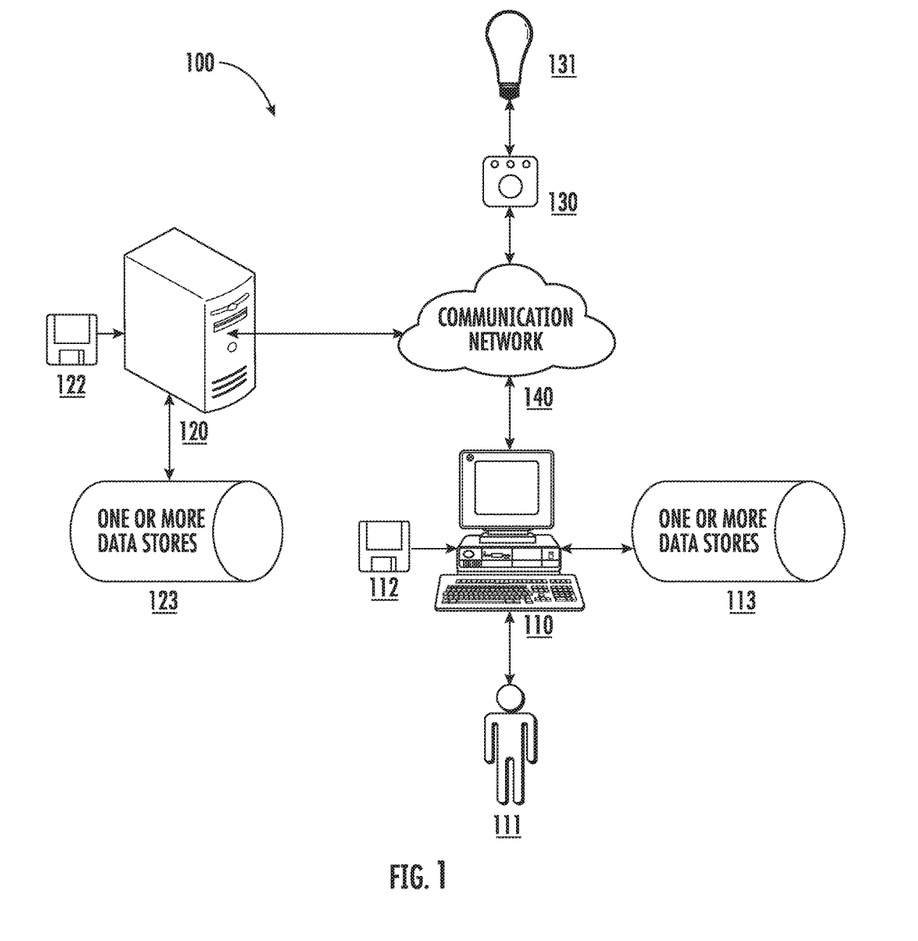
FIG. 1 illustrates an implementation of a system in accordance with the subject matter of this disclosure.

An implementation of a system 100 for providing notification about a status of a patient examination is illustrated in FIG. 1. The system 100 comprises at least one visual indicator 131 configured to provide notification about the status of a patient examination, at least one control device 130 in operative communication with the at least one visual indicator 131, one or more data stores 113, 123, one or more processors 110, 120 in operative communication to the one or more data stores 113, 123 and the at least one control device 130, and one or more computer-readable media 112, 122 upon which is encoded machine-readable code that when executed is configured so that the system 100 carries out one or more methods for providing notification about the status of a patient examination.

The at least one control device 130 is configured to change the one or more control parameters of the at least one visual indicator 131 based on a signal indicative of the patient examination status so as to cause the at least one visual indicator 131 to reflect the status of the patient examination in real-time or in substantially real-time (i.e., as data comprising information indicative of the status of the patient examination is received and stored), or asynchronously (e.g., every thirty seconds, every five minutes, or every hour, etc.). Examples of suitable control devices 130 include without limitation a specialized computing device; a generic computing device such as a tablet, smart phone, personal computer; or a lighting control device such as a Hue Bridge available from Philips Lighting Holding B.V. The at least one control device 130 may communicate with the at least one visual indicator wirelessly (via WiFi, Bluetooth, ZigBee, or other suitable technology known in the art), via power line carrier signal, or by another means, as understood by those skilled in the art.

Figure 3:
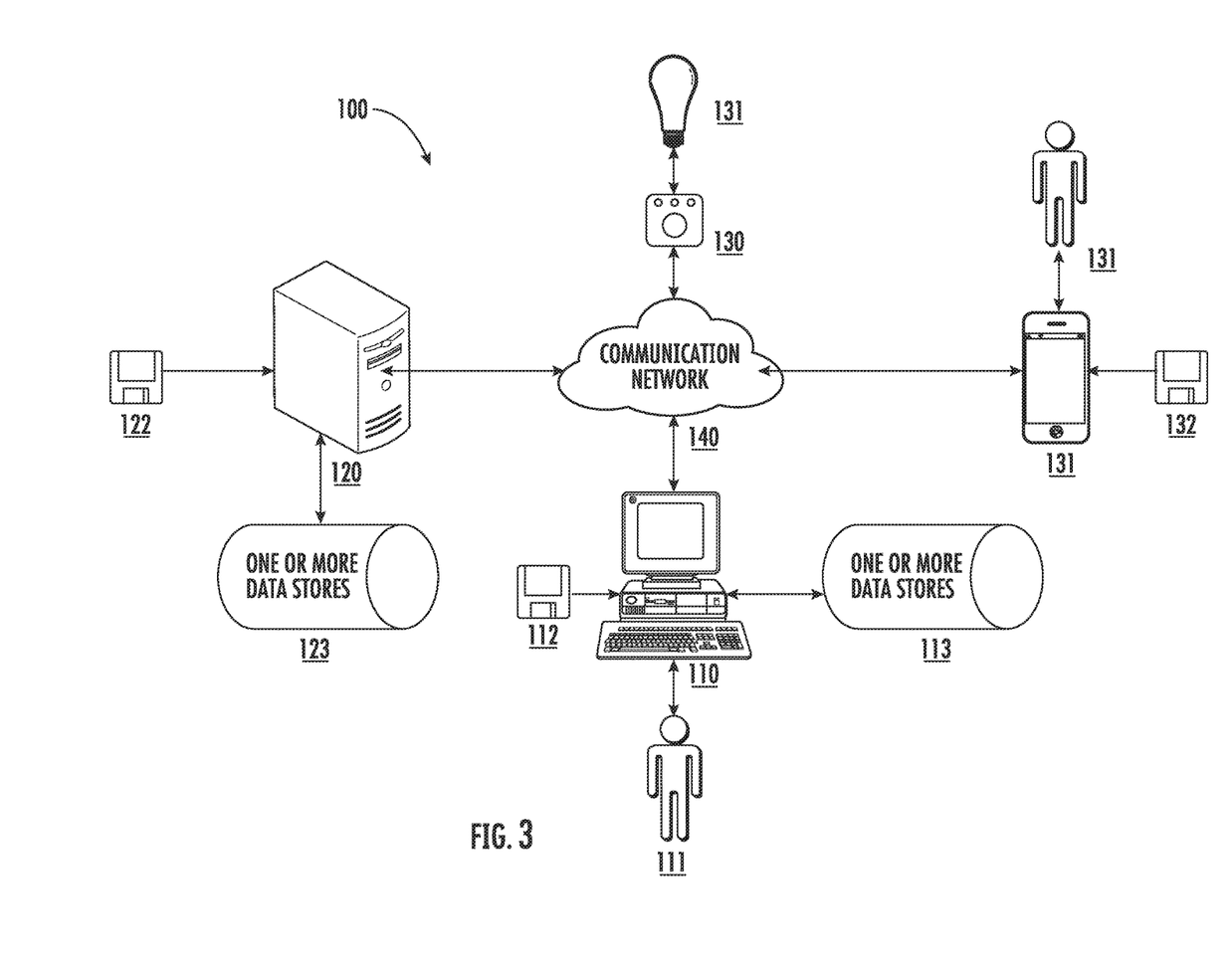
FIG. 3 illustrates a system diagram of an implementation of a system in accordance with the subject matter of this disclosure.

As shown in FIG. 1 and FIG. 3, the at least one visual indicator 131 may comprise one or more light sources. The one or more light sources can be one or more smart light bulbs including integral circuitry to control various parameters such as the intensity and/or hue (color) of their light output. Smart light bulbs also include circuitry to communicate with the at least one control device 130. It should be appreciated that the body of the smart bulb could include the at least one control device 130 as an integral or separate component. As another example, the one or more light sources can be conventional light bulbs such as incandescent bulbs, fluorescent bulbs, LED bulbs, or any other bulbs known to those skilled in the art and not incorporating both the communication and control circuitry attributed to smart bulbs above. Thus, for light sources, examples of control parameters include without limitation the operation (on/off), intensity, and/or hue (color) of the one or more light sources.

In another aspect and as illustrated in FIG. 3, the at least one visual indicator 131 may comprise one or more electronic devices 131 capable of providing an output response based on the signal indicative of the patient examination status (e.g., audio alert, a text message or status message about current status of a patient examination displayed on an electronic display of the electronic device, and so forth). The one or more electronic devices may be utilized alone or in combination with the one or more light sources.

Examples of suitable electronic devices 131 include without limitation a desktop computer, laptop computer, tablet, smart phone, personal digital assistant, smart watch, and so forth. In this manner, a physician or other medical practice personnel may receive the status of the patient examination without being in a direct line of sight of the examination room. For example, a physician, while out of the office for lunch, could check his or her smart watch or smart phone to see if a patient is ready for examination and evaluation by the physician. It should be appreciated that the one or more electronic devices may be used instead of or in combination with the one or more light sources described above.

The computer-readable media 112, 122, 132 upon which is encoded machine-readable code should be suitable for storing computer program instructions and data, which may be same as or different from the one or more data stores 113, 123. The computer-readable media 112, 122, 132 and one or data stores 113, 123 may include tangible non-transitory computer-readable storage media, which may include hard drives, floppy diskettes, optical disks, CD-ROMs, DVDs, read-only memories (ROMs), random access memories (RAMs), EPROMs, EEPROMs, flash memory, magnetic or optical cards, solid-state memory devices, or other types of storage media suitable for storing electronic instructions. In addition, in some implementations, the computer-readable media 112, 122, 132 and one or data stores 113, 123 may include a transitory computer-readable signal (in compressed or uncompressed form). Examples of computer-readable signals, whether modulated using a carrier or not, include, but are not limited to, signals that a computer system hosting or running a computer program can be configured to access, including signals downloaded through the Internet or other suitable networks.

The one or more processors 110, 120, 130 suitable for the execution of a computer program may include both general and special purpose microprocessors, and any one or more processors of any kind of digital computer. In general, the one or more processors 110, 120, 130 receive instructions and data from a read-only memory or a random access memory or both. The one or more processors 110, 120, 130 may be present as an electronic device, such as a desktop computer, laptop computer, tablet, smart phone, personal digital assistant, netbook, and so forth. The essential elements of such electronic devices are one or more processors 110, 120, 130 for performing instructions and one or more computer-readable media 112, 122, 132 upon which is encoded machine-readable code that when executed is configured so that the computer carries out one or more methods. The electronic device may also have a user interface that allows a user 111 to enter information indicative of the status of the patient examination. The user interface may be a graphical user interface, an audio only interface, a multi-mode interface, or any other interface for interacting with the user.

It should be appreciated that the one or more processors 110, 120, 130 may communicate with the at least one control device 130 through least one communication network (e.g., a laptop computer communicating with the at least one control device). Similarly, the at least one control device 130 can communicate with at least one visual indicator 131 through at least one communication network 140. Suitable communication networks include without limitation an intranet, the Internet, a cellular network, a local area network (LAN), or any other such network or combination, and communication over the network can be enabled via wired and/or wireless connections.

Figure 4:
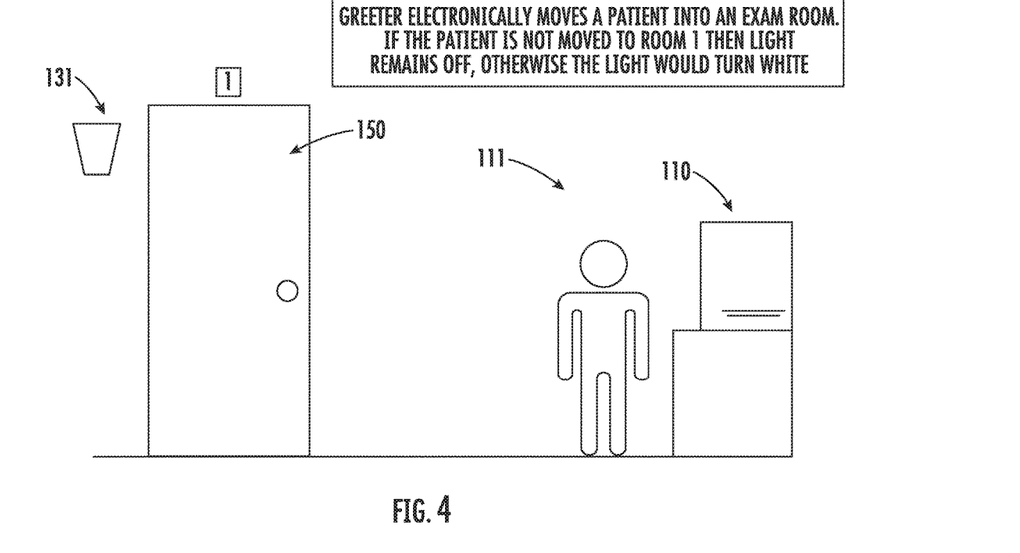
FIG. 4 illustrates an example environment in which a system may be employed in accordance with the subject matter of this disclosure
Figure 5:
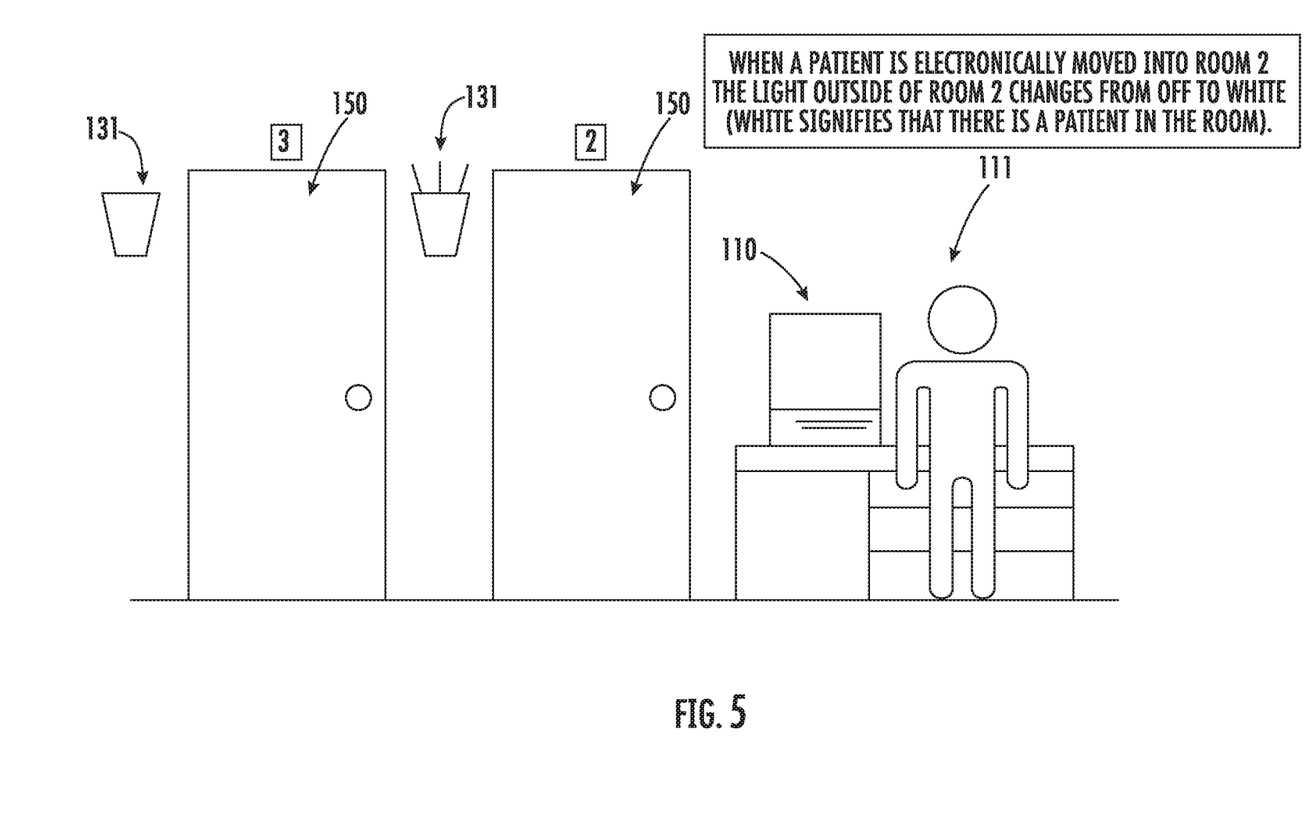
FIG. 5 illustrates an example environment in which a system may be employed in accordance with the subject matter of this disclosure.
Figure 6:
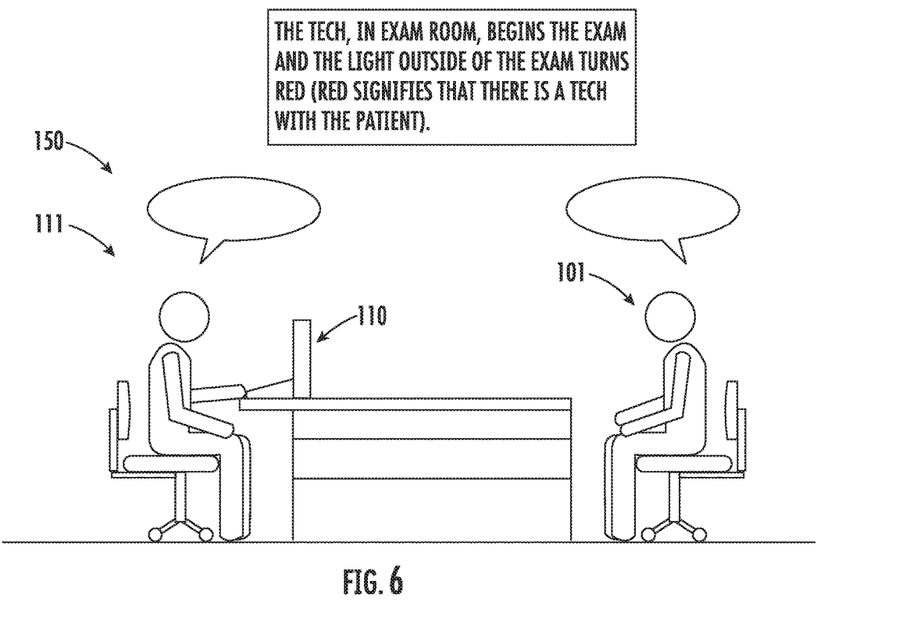
FIG. 6 illustrates an example environment in which a system may be employed in accordance with the subject matter of this disclosure.
Figure 7:
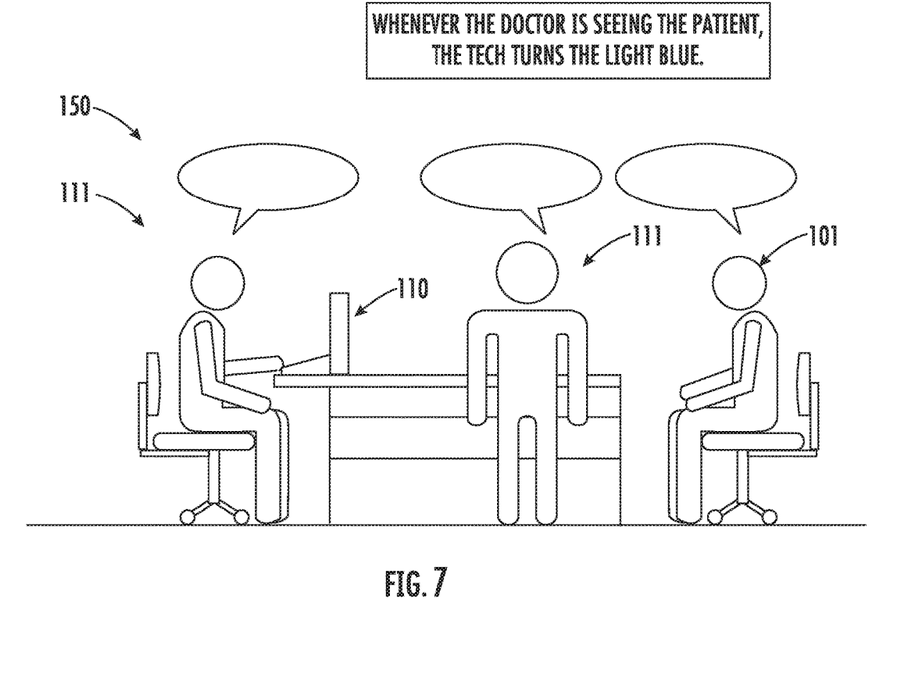
FIG. 7 illustrates an example environment in which a system may be employed in accordance with the subject matter of this disclosure.

FIGS. 4-7 illustrate an example of an environment in which the systems and methods of the invention may be employed. The environment illustrated is a medical office including one or more patient examination rooms 150 with each patient examination room 150 having a corresponding visual indicator 131. The visual indicator 131 may be positioned outside of the patient examination room 150, for example, one or more light sources secured to a support outside of the patient examination room as shown in FIGS. 4-5.

As another example, the at least one visual indicator 131 may comprise a plurality of light sources. For example, the visual indicator may comprise four conventional light bulbs positioned in a vertical or horizontal manner outside the door of the patient examination room. Each conventional light bulb can be associated with a particular status of the patient examination.

2. Method for Providing Visual Notification about the Status of a Patient Examination and Tangible Non-Transitory Computer Readable Storage Medium It should be appreciated that the methods described in this disclosure may be implemented in hardware, software, or a combination thereof. In the context of software, the described operations represent computer-executable instructions stored on one or more computer-readable media 111, 121, 131 that, when executed by one or more processors 110, 120, perform the recited operations. Generally, computer-executable instructions include routines, programs, objects, components, data structures, and the like that perform particular functions or implement particular abstract data types. The order in which the operations are described is not intended to be construed as a limitation, and any number of the described operations can be combined in any order and/or in parallel to implement the method.

Figure 2:
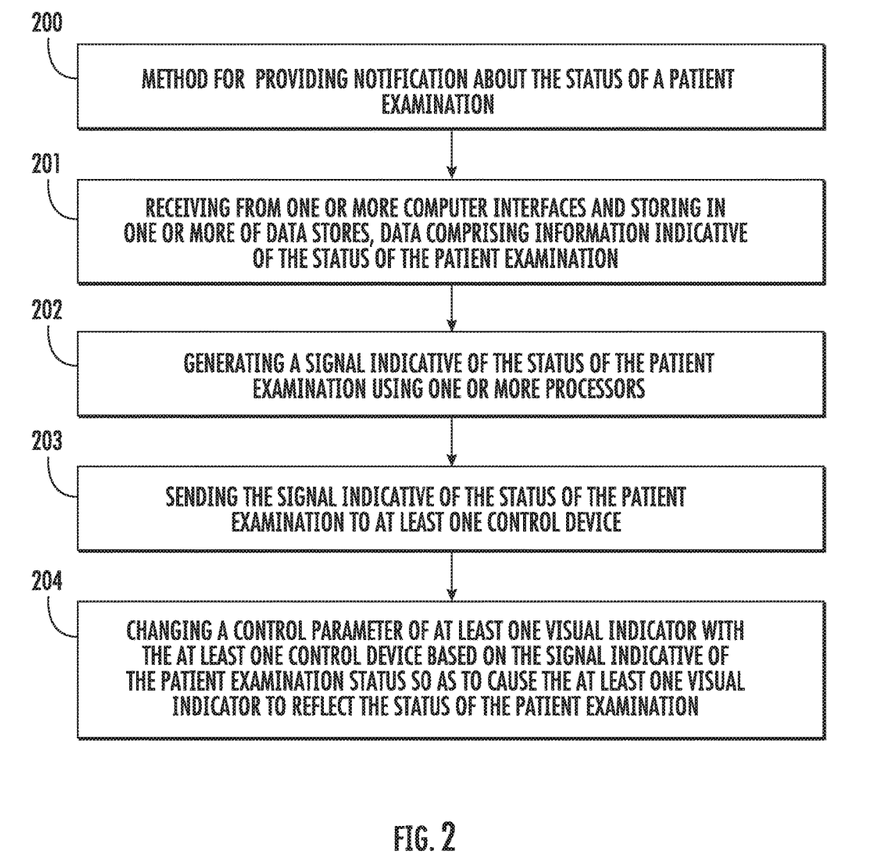
FIG. 2 illustrates a flow diagram for an implementation of a method in accordance with the subject matter of this disclosure.

FIG. 2 depicts a flow diagram of an example method for providing notification about the status of a patient examination at 200. The method 200 carried out by the system comprises at least the following steps:

receiving from one or more computer interfaces and storing in one or more data stores, data comprising information indicative of the status of the patient examination 201;

generating a signal indicative of the status of the patient examination using one or more processors 202;

sending the signal indicative of the status of the patient examination to at least one control device over at least one communication network using the one or more processors 203; and changing a control parameter of at least one visual indicator based on the signal indicative of the patient examination status using the at least one control device so as to cause the at least one visual indicator to reflect the status of the patient examination 204.

As illustrated in FIGS. 4-7, a user 111 enters data comprising information indicative of the status of the patient examination using one or more computer interfaces in operative communication with the one or more processors, e.g., an electronic device such as a desktop or laptop computer. Once the user 111 enters the data comprising information indicative of the status of the patient examination (e.g., data may be entered into a medical records program and stored in a database), the system 100 stores the information in the one or more data stores 113, 123. It should be appreciated that the one or more data stores 113, 123 may be located on computer-readable media associated with the one or more processors, for example, on computer-readable media (e.g., a hard drive) of the electronic device, and/or computer-readable media in a separate, remote location, for example, on computer-readable media on a remote server accessed over the communication network (e.g., the Internet). Non-limiting examples of information indicative of the status of the patient examination may include:

| Information Indicative of the Status of the Patient Examination |
| --- |
| Patient Examination Room Assigned to a Patient |
| Patient in Patient Examination Room Alone |
| Patient in Patient Examination Room with a Technician and/or Nurse |
| Vital Check of Patient in Patient Examination Room Completed |
| Medical History of Patient in Patient Examination Room Completed |
| Patient in Patient Examination Room with a Physician |

Using the one or more processors of the electronic device, the system 100 generates a signal indicative of the status of the patient examination, and sends the signal to the at least one control device 130 over the communication network 140. The system 100 generates and sends the signal (in real-time, in substantially real-time, or asynchronously) as the data comprising information indicative of the status of the patient examination is stored in the one or more data stores. The signal sent to the at least one control device 130 corresponds to the information indicative of the status of the patient examination. Based on the signal, the at least one control device 130 changes one or more of the control parameters of the at least one visual indicator 131 so as to cause the at least one visual indicator 131 to reflect the status of the patient examination in real-time, in substantially real-time, or asynchronously. In this manner, the system 100 can help increase the accuracy of patient medical records by ensuring that a patient medical record is being updated contemporaneously with the patient examination and not at a later time, e.g., after the patient examination is completed. If the patient medical record is updated after the patient examination is complete, it can contain errors because it might be entered based on a person's inaccurate recollection, not include certain data at all, and so forth.

Although the system 100 may cause the at least one visual indicator 131 to reflect the status of the patient examination in real-time, in substantially real-time, or asynchronously, it should be appreciated that manual operation may be desired in some scenarios. Accordingly, the system may also be configured for manual operation. For example, the user interface can include an option for receiving a manual input (e.g., mouse click, keyboard entry, voice command, and so forth) from a user 111 that causes the at least one visual indicator to 131 to reflect the status of the patient examination in real-time, in substantially real-time, or asynchronously.

In a system utilizing one or more smart bulbs as the at least one visual indicator, the control device may be configured to change certain parameters of the visual indicator, for example, the hue and operational status of each smart bulb corresponding to a patient examination room as follows:

TABLE 2

| Information Indicative of the Status of the Patient Examination | |
| --- | --- |
| Information Indicative of the Status of the Patient Examination | Parameter(s) of Visual Indicator |
| Patient Examination Room Empty | Status = Off |
| | Hue = N/A |
| Patient Assigned to Patient Examination Room | Status = On |
| | Hue = White |
| Patient in Patient Examination Room with a Technician and/or Nurse | Status = On |
| | Hue = Red |
| Vital Check of Patient in Patient Examination Room Completed | Status = On |
| | Hue = Orange |
| Medical History of Patient in Patient Examination Room Completed and Patient Ready for Physician | Status = On |
| | Hue = Green |
| Patient in Patient Examination Room with a Physician | Status = On |
| | Hue = Blue |

Thus, if a user 111 (e.g. a technician, administrative staffer, nurse, physician, and so forth) assigns a patient to a patient examination room 150 using the one or more computer interfaces on the electronic device, the system 100 stores such information in the one or more data stores and sends a signal to the at least one control device. Based on the signal from the system, the control device turns the visual indicator on and ensures that the hue of the visual indicator is white. Similarly, if the user 111 later completes a vital check for a patient and enters the information for the patient gathered from the vital check into the system 100 using the electronic device, the system 100 stores such information in the one or more data stores and the system 100 sends a signal to the at least control device 100. Using the signal from the system, the at least one control device 130 ensures the visual indicator 131 is on and that the hue of the visual indicator 131 is orange.

The above examples illustrate a particular implementation of a system 100 for providing notification about the status of a patient examination. It should be appreciated that this example is merely to illustrate the calculations undertaken by the system and method of one embodiment of the invention, and is not intended to limit the scope of the invention in any way.

While this specification contains many specific implementation details and may describe particular embodiments of the subject matter in great detail, these should not be construed as limitations on the scope of any invention or of what may be claimed, but rather as descriptions of features that may be specific to particular embodiments of particular inventions. Other embodiments are within the scope of the following claims. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub-combination or variation of a sub-combination. It of course will be appreciated that in the development of such an actual implementation, numerous implementation-specific decisions must be made to achieve the developers' specific goals, such as compliance with system-related and economic-related constraints, which may vary from one implementation to another. Moreover, it will be appreciated that while such a development effort might be complex and time-consuming, it would nevertheless be a routine undertaking for those of ordinary skill in the art having the benefit of this disclosure. Therefore, the foregoing description is not intended to limit, and should not be construed as limiting, the invention to the particular exemplifications presented herein.

Similarly, while operations are depicted in the drawings in a particular order, this should not be understood as requiring that such operations be performed in the particular order shown or in sequential order, or that all illustrated operations be performed, to achieve desirable results. For example, the processes depicted in the accompanying figures do not necessarily require the particular order shown, or sequential order, to achieve desirable results. In certain circumstances, multitasking and parallel processing may be advantageous. Moreover, the separation of various system components in the embodiments described above should not be understood as requiring such separation in all embodiments, and it should be understood that the described program components and systems generally can be integrated together in a single software product or packaged into multiple software products.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text taken in context clearly indicates otherwise.

Each and every patent or other publication or published document referred to in any portion of this specification is incorporated as a whole into this disclosure by reference, as if fully set forth herein.

What is claimed is:

1. A system for providing a visual notification of a status of a patient examination, the system comprising:
   a) at least one visual indicator;
   b) at least one control device in operative communication with the at least visual indicator;
   c) one or more data stores;
   d) one or more processors in operative communication with the one or more data stores and the at least one control device; and
   e) one or more tangible non-transitory computer readable storage media upon which is encoded machine-readable code that when executed is configured so that the system carries out a method comprising:
      receiving from one or more computer interfaces and storing in one or more of the data stores, data comprising information indicative of the status of the patient examination;
      generating a signal indicative of the status of the patient examination using the one or more processors;
      sending the signal indicative of the status of the patient examination to the at least one control device over at least one communication network using the one or more processors; and
      changing a control parameter of the at least one visual indicator based on the signal indicative of the status of the patient examination using the at least one control device so as to cause the at least one visual indicator to reflect the status of the patient examination;
      wherein the data comprising information indicative of the status of the patient examination is obtained or derived from an electronic medical record; and
      wherein the status of the patient examination is relative to the stage of the patient examination in the examination room.

2. The system of claim 1 wherein the at least one visual indicator comprises one or more light sources.

3. The system of claim 2 wherein the at least one control device is configured to control the hue of light emitted by the one or more light sources, based on the signal indicative of the status of the patient examination.

4. The system of claim 2 wherein the at least one visual indicator is positioned outside of a patient examination room.

5. The system of claim 2 wherein the at least one visual indicator reflects the status of the patient examination in real-time or in substantially real-time.

6. The system of claim 1 wherein the visual indictor comprises one or more electronic devices.

7. The system of claim 2 wherein the at least one visual indicator further comprises one or more electronic devices.

8. A tangible non-transitory computer readable storage medium having computer executable code thereon comprising a method for providing a visual notification of a status of a patient examination, the method comprising:

receiving from one or more computer interfaces and storing in one or more data stores, data comprising information indicative of the status of the patient examination;

generating a signal indicative of the status of the patient examination using one or more processors;

sending the signal indicative of the status of the patient examination to at least one control device over at least one communication network using the one or more processors; and changing a control parameter of at least one visual indicator based on the signal indicative of the status of the patient examination using the at least one control device so as to cause the at least one visual indicator to reflect the status of the patient examination;

wherein the data comprising information indicative of the status of the patient examination is obtained or derived from an electronic medical record; and wherein the status of the patient examination is relative to the stage of the patient examination in the examination room.

9. The tangible non-transitory computer readable storage medium of claim 8 wherein the at least one visual indicator comprises one or more light sources.

10. The tangible non-transitory computer readable storage medium of claim 9 wherein the at least one control device is configured to control the hue of light emitted by the one or more light sources, based on the signal indicative of the status of the patient examination.

11. The tangible non-transitory computer readable storage medium of claim 10 wherein the at least one visual indicator is positioned outside of a patient examination room.

12. The tangible non-transitory computer readable storage medium of claim 9 wherein the at least one visual indicator reflects the status of the patient examination in real-time or in substantially real-time.

13. The tangible non-transitory computer readable storage medium of claim 8 wherein the visual indictor comprises one or more electronic devices.

14. A method for providing a visual notification of a status of a patient examination, the method comprising:

receiving from one or more computer interfaces and storing in one or more data stores, data comprising information indicative of the status of the patient examination;

generating a signal indicative of the status of the patient examination using one or more processors;

sending the signal indicative of the status of the patient examination to at least one control device over at least one communication network using the one or more processors; and changing a control parameter of at least one visual indicator based on the signal indicative of the status of the patient examination using the at least one control device so as to cause the at least one visual indicator to reflect the status of the patient examination;

wherein the data comprising information indicative of the status of the patient examination is obtained or derived from an electronic medical record; and wherein the status of the patient examination is relative to the stage of the patient examination in the examination room.

15. The method of claim 14 wherein the at least one visual indicator comprises one or more light sources.

16. The method of claim 15 wherein the at least one control device is configured to control the hue of light emitted by the one or more light sources, based on the signal indicative of the status of the patient examination.

17. The method of claim 16 wherein the at least one visual indicator is positioned outside of a patient examination room.

18. The method of claim 14 wherein the at least one visual indicator reflects the status of the patient examination in real-time or in substantially real-time.

19. The method of claim 14 wherein the visual indictor comprises one or more electronic devices.

20. The system of claim 1 wherein the at least one visual indicator reflects the status of the patient examination in real-time or in substantially real-time.

* * * * *